US007842454B2

(12) United States Patent
Shomi et al.

(10) Patent No.: US 7,842,454 B2
(45) Date of Patent: Nov. 30, 2010

(54) KIT FOR PREPARING CANCER CELL DETECTION SAMPLE AND KIT FOR CANCER CELL DETECTION USING THE SAME

(75) Inventors: Keiichiro Shomi, Kobe (JP); Tomokazu Yoshida, Kobe (JP)

(73) Assignee: Sysmex Corporation, Hyogo (JP)

( * ) Notice: Subject to any disclaimer, the term of this patent is extended or adjusted under 35 U.S.C. 154(b) by 603 days.

(21) Appl. No.: 11/802,830

(22) Filed: May 25, 2007

(65) Prior Publication Data

US 2007/0287149 A1 Dec. 13, 2007

(30) Foreign Application Priority Data

May 30, 2006 (JP) ............................ 2006-150753

(51) Int. Cl.
*B65D 39/00* (2006.01)
*C12Q 1/70* (2006.01)

(52) U.S. Cl. ............................ 435/5; 215/247; 215/249

(58) Field of Classification Search ....................... None
See application file for complete search history.

(56) References Cited

U.S. PATENT DOCUMENTS

2006/0067890 A1 3/2006 Fujiwara et al.
2006/0239967 A1 10/2006 Fujiwara et al.

*Primary Examiner*—Mary E Mosher
*Assistant Examiner*—Stuart W Snyder
(74) *Attorney, Agent, or Firm*—Sughrue Mion, PLLC

(57) ABSTRACT

A kit for preparing a cancer cell detection sample which is highly safe, simple, and high in precision, and can detect a cancer cell quantitatively, and a kit for cancer cell detection using the same, as well as a method for diagnosing cancer using those kits, and a method for preparing a sample for cancer cell detection are provided. A kit for preparing a detection sample for detecting a cancer cell of the present invention, comprising a test container having an opening for receiving a biological sample collected from a subject, and a reagent inclusion part for accommodating a reagent containing a virus, a seal part for sealing the reagent inclusion part of the test container, a cap for closing the opening, and an opener for breaking the seal part.

19 Claims, 9 Drawing Sheets

KIT FOR PREPARING CANCER CELL DETECTION SAMPLE AND KIT FOR CANCER CELL DETECTION USING THE SAME

FIELD OF THE INVENTION

The present invention relates to a kit for preparing a cancer cell detection sample and a kit for cancer cell detection using the same.

BACKGROUND

Cancer is a primary cause for mortality of Japanese, and it is said that if early treatment by early diagnosis is possible, the mortality can be remarkably decreased.

Currently, diagnosis of cancer is performed by discriminating a normal cell and a cancer cell by a morphological test of a cell in a test sample collected from a subject with microscopic examination generally by a cell testing technician. However, since this diagnosis method is a visual test by a cell testing technician, the method is not suitable for handling of a large amount of test samples as in group medical examinations, and there is a problem that unevenness occurs in test results depending on the status of a test sample, and the sample cannot be analyzed quantitatively.

In addition, a method for diagnosing cancer by detecting a tumor-derived DNA in plasma and serum of a subject is also being studied. Specifically, cancer is diagnosed by concentrating cells contained in blood collected from a subject, and biochemically analyzing a DNA and the like related to a blood free cancer cell in the concentrated cells. This method can relatively safely treat a large amount of test samples, but there is a problem that a step of concentrating blood free cancer cells is difficult, and simplicity is lacked.

On the other hand, in recent years, an anti-cancer agent (US2006239967) and a cancer cell detection reagent (US2006067890) using an oncolytic virus which specifically grows in a cancer cell are reported. The oncolytic virus is a virus which specifically grows in a cancer cell and, by infecting a cancer cell with the virus, the cancer cell can be directly destroyed and killed and, by incorporating a gene of a target protein into a genome thereof, it becomes possible to simply detect a cancer cell.

However, since the oncolytic virus has infectivity also on a normal cell apart from simple detection of a cancer cell, a facility at a P2 level becomes necessary for the detection. Therefore, there is a problem that it is difficult to actually use the virus in group medical examinations or the like.

SUMMARY

The scope of the present invention is defined solely by the appended claims, and is not affected to any degree by the statements within this summary.

In view of such circumstances, the present inventors intensively studied and, as a result, found out a kit for preparing a cancer cell detection sample used in detection of a cancer cell with a reagent containing a virus, particularly, an oncolytic virus, which is not accompanied by contamination due to diffusion of the virus to the outside, which resulted in completion of the present invention.

That is, the present invention provides:

(1) A kit for preparing a detection sample for detecting a cancer cell, comprising a test container having an opening for receiving a biological sample collected from a subject, and a reagent inclusion part for accommodating a reagent containing a virus, a seal part for sealing the reagent inclusion part of the test container, a cap for closing the opening, and an opener for breaking the seal part;

(2) The kit for preparing a detection sample according to (1), wherein the cap has a virus-impermeable breathable filter;

(3) The kit for preparing a detection sample according to (1), wherein the opener breaks the seal part accompanying with an action of closing the opening by the cap;

(4) The kit for preparing a detection sample according to (1), wherein the cap has the opener;

(5) The kit for preparing a detection sample according to (1), wherein the virus in an interior portion of the test container is isolated from the outside when the opener breaks the seal part;

(6) The kit for preparing a detection sample according to (1), wherein the cap and the opener are integrally configured, the opener has a leading edge for breaking the seal part, and a middle part for connecting the cap and the leading edge, and the middle part is configured so as to be inserted into the opening in the state where it is adhered to the opening;

(7) The kit for preparing a detection sample according to (1), wherein a genome of the virus comprises a promoter of a carcinogenic gene and a gene encoding a target protein;

(8) The kit for preparing a detection sample according to (1), wherein the virus is an oncolytic virus;

(9) The kit for preparing a detection sample according to (1), wherein the virus is d12.CALP, d12.CALP delta RR, Telomelysin, Telomelysin-RGD, AxE1AdB-UPRT, AdSLP1.E1AdB, AxE1CAUP, AdE3-IAI.3B, Ad-MKAdMK, AdCEAp/Rep, AdAFPep/Rep, MMP-sub II SeV/delta M, or CD-MMP-sub II-SeV/delta M;

(10) The kit for preparing a detection sample according to (1), wherein the sample is collected from blood, sputum or uterus;

(11) A method for diagnosing cancer, comprising using the kit for preparing a detection sample as defined in (1);

(12) The diagnosis method according to (11), wherein the cancer is blood cancer, lung cancer or uterine cervical cancer;

(13) A kit for detecting a cancer cell, comprising a kit for preparing a detection sample for detecting a cancer cell comprising a test container having an opening for receiving a biological sample collected from a subject, and a reagent inclusion part for accommodating a reagent containing a virus, a seal part for sealing the reagent inclusion part of the test container, a cap for closing the opening, and an opener for breaking the seal part, and a slide glass comprising an insertion part for inserting the test container, a second opener for breaking a bottom of the test container by an action of inserting the test container into the insertion part, and a holding part for guiding a reaction solution of the biological sample and the reagent from the test container in which a bottom is broken with the second opener, and observably holding the reaction solution from the outside;

(14) The kit for cancer cell detection according to (13), wherein the cap has a virus-impermeable breathable filter;

(15) The kit for cancer cell detection according to (13), wherein the opener breaks the seal part accompanying with an action of closing the opening with the cap;

(16) The kit for cancer cell detection according to (13), wherein a virus in the interior portion is isolated from the outside when the second opener breaks the bottom of the test container;

(17) The kit for cancer cell detection according to (13), wherein a bottom of the test container has a second seal part which is broken with the second opener;

(18) A method for diagnosing cancer, comprising using the kit according to claim 13 for detection;

(19) The diagnosis method according to (18), wherein the cancer is blood cancer, lung cancer or uterine cervical cancer;

(20) A method for preparing a sample for detecting a cancer cell comprising steps of, adding a sample collected from a subject to a test container having an opening, and a reagent inclusion part for accommodating a reagent containing a virus in the state where it is sealed with a seal part, closing the opening with a cap, and breaking the seal part with an opener.

According to the present invention, since a reagent containing a virus is mixed and reacted with a sample without being diffused to the outside, and it becomes possible to observe the sample after the reaction, a kit for preparing a cancer cell detection sample which is highly safe, simple, and high in precision, and can detect a cancer cell quantitatively, and a kit for cancer cell detection using the same, as well as a method for diagnosing cancer using those kits, and a method for preparing a sample for cancer cell detection are provided.

When the kit and the method of the present invention are used, since it is not necessary to provide a large scale test facility at a P2 level, a group medical examination of cancer which is simple and high in precision becomes possible.

BRIEF DESCRIPTION OF THE DRAWINGS

FIG. 7(*b*) shows a cross-sectional view (b) of the slide glass for microscopic examination shown in FIG. 6.

DETAILED DESCRIPTION OF THE EMBODIMENT

Figure 1:
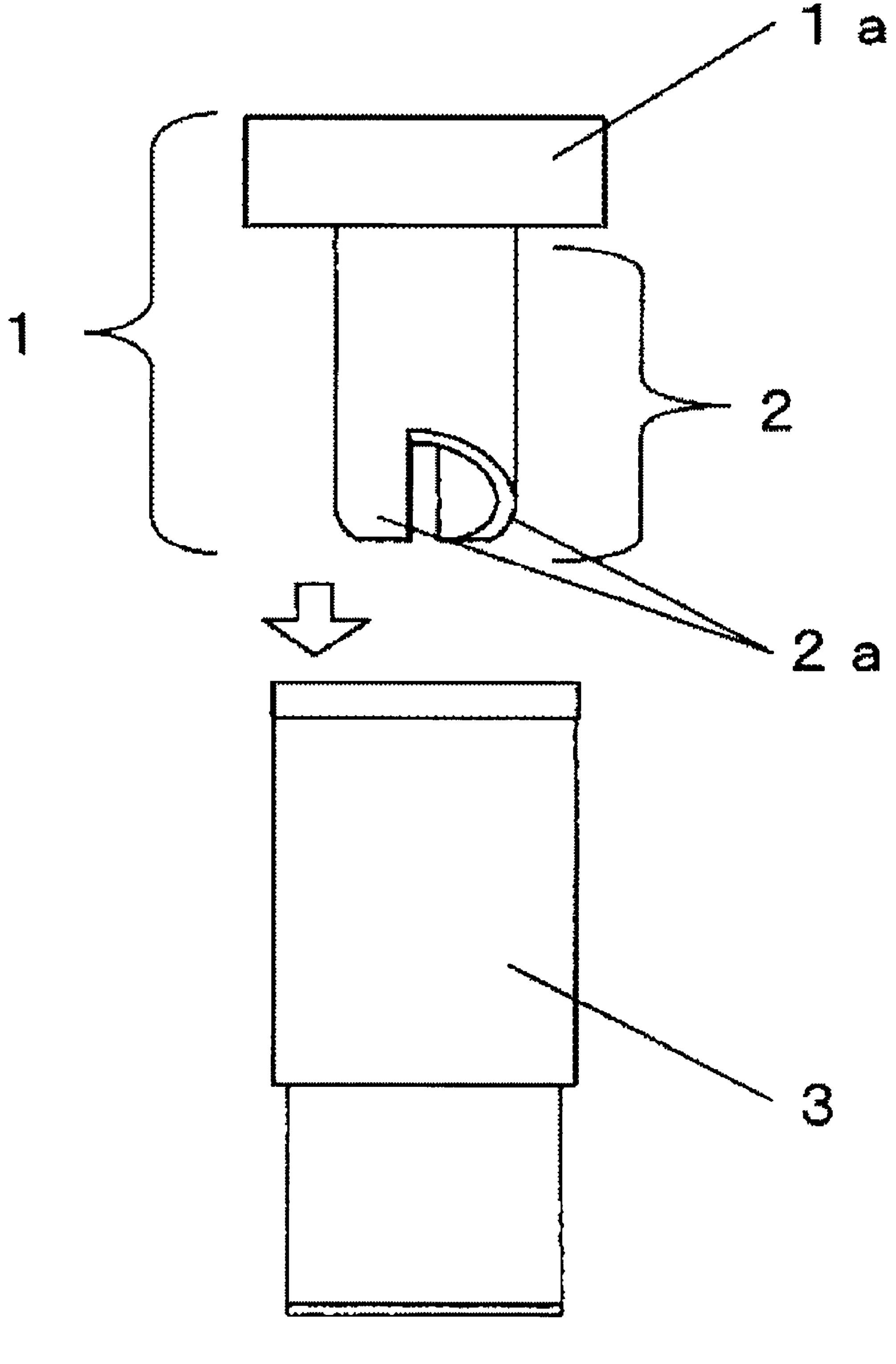
FIG. 1 is a side view showing a test container and a cap which are one embodiment of the present invention.
Figure 2:
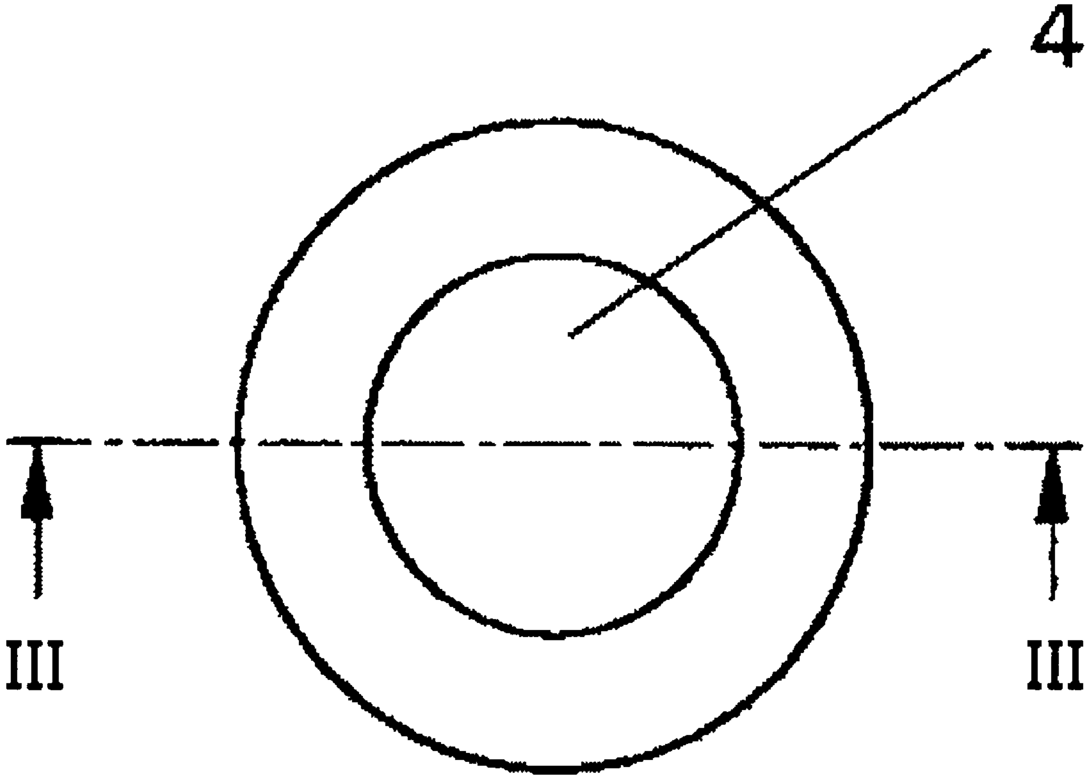
FIG. 2 is a top view of the test container shown in FIG. 1.

First, a construction of the kit for preparing a cancer cell detection sample relating to the present embodiment will be explained. FIG. 1 is a side view showing a kit for preparing a cancer cell detection sample relating to one embodiment. The kit for preparing a cancer cell detection sample relating to the present embodiment includes a cap 1 and a test container 3. The test container 3 is configured to be substantially cylindrical and, on an upper side thereof, as shown in FIG. 2, an opening 4 for receiving a biological sample collected from a subject is provided. The cap 1 which is inserted through the opening 4 includes an opener 2 which is substantially cylindrical, and a disk-like jaw part 1*a* provided on an upper end of the opener 2. Further, the jaw part 1*a* has a fitting part lb which fits with an entire circumference of an upper end edge of the test container 3 when the cap 1 is abutted against the test container 3 (see FIG. 5). The opener 2 has substantially the same diameter as an upper side inner side of the test container 3, that is, a diameter of the opening 4. Therefore, such opener 2 is inserted until the jaw part 1*a* is abutted against an upper end of the test container 3, in the state where the opener 2 is adhered to an entire circumference of the opening 4 of the test container 3. In addition, two protrusions 2*a* are provided on a lower side of the cylindrical opener 2, that is, on a side opposite to the jaw of the cap 1, and a first aluminum sheet 5 described later can be opened with this protrusion 2*a*. In addition, at a central part of the cap 1, a virus-adsorbable charcoal filter 10 is provided so as to close a cavity of the opener 2. Thereby, also when the test container 3 is closed with the cap 1, breathing into an interior space of the test container 3 from the outside air can be maintained (see FIG. 5).

Figure 3:
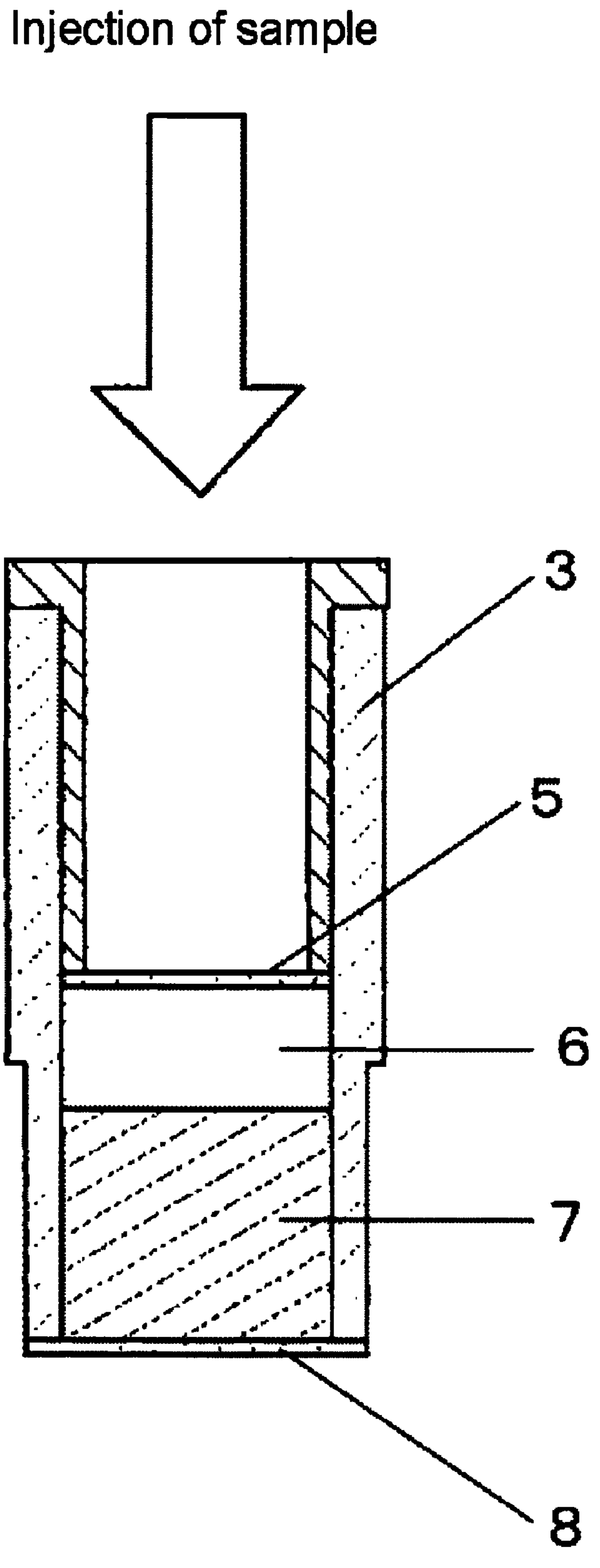
FIG. 3 is an A-A cross-sectional view of FIG. 2, in the test container shown in FIG. 1.

FIG. 3 is an III-III cross-sectional arrow view shown in FIG. 2, of the test container 3. In the present embodiment, in the test container 3, the first aluminum sheet 5 partitioning the interior portion of the container is provided approximately at a center of the interior portion of the container. Further, on a bottom of the test container 3, a second aluminum sheet 8 is provided, and a space held by the first aluminum sheet 5 and the second aluminum sheet 8 is a reagent inclusion part 6 isolated from the outside. In this reagent inclusion part 6, a reagent 7 containing a virus is sealed therein. Like this, since the reagent 7 is sealed in the reagent inclusion part 6 which is a space isolated with the first aluminum sheet 5 and the second aluminum sheet 8, the test container 3 can be carried safely without diffusion of a virus to the outside.

Figure 4:
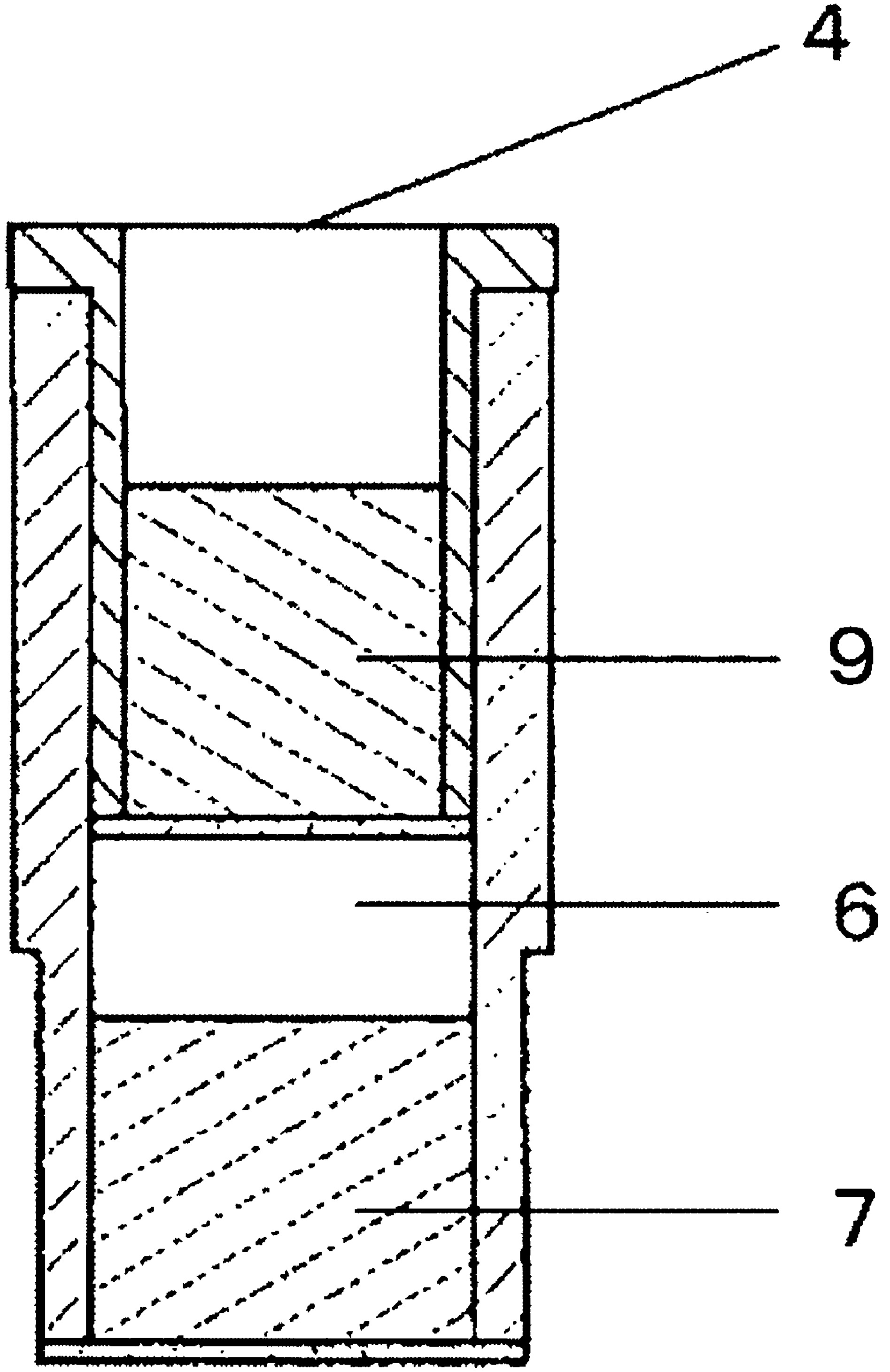
FIG. 4 is a side cross-sectional view showing the test container of FIG. 1 in the state where a sample is injected.

Then, a motion when a cancer cell detection sample is prepared using the kit for preparing a cancer cell detection sample relating to the present embodiment will be explained. First, a user injects a sample into the test container 3. A cross-sectional view of the test container 3 into which a sample is injected is shown in FIG. 4. With the aforementioned construction, a part from the opening 4 of the test container 3 (upper end) to an approximately central position of the test container 3, partitioned with the first aluminum sheet 5 (i.e. an upper side part of the test container 3) is concave, and a sample 9 can be accommodated therein. The user injects the sample into a concave part of the test container 3, for example, by using a pipette. The sample 9 injected through the opening 4 of the test container 3 is dammed with the first aluminum sheet 5 provided at a center of the test container, at the center of the interior of the container. For this reason, at injection of the reagent, it is not mixed with the reagent 7 containing a virus sealed into the aforementioned reagent inclusion part 6. That is, at injection of the sample, the reagent 7 containing a virus is in the sealed state where it is isolated from the outside, and diffusion of the virus to the outside does not occur.

Figure 5:
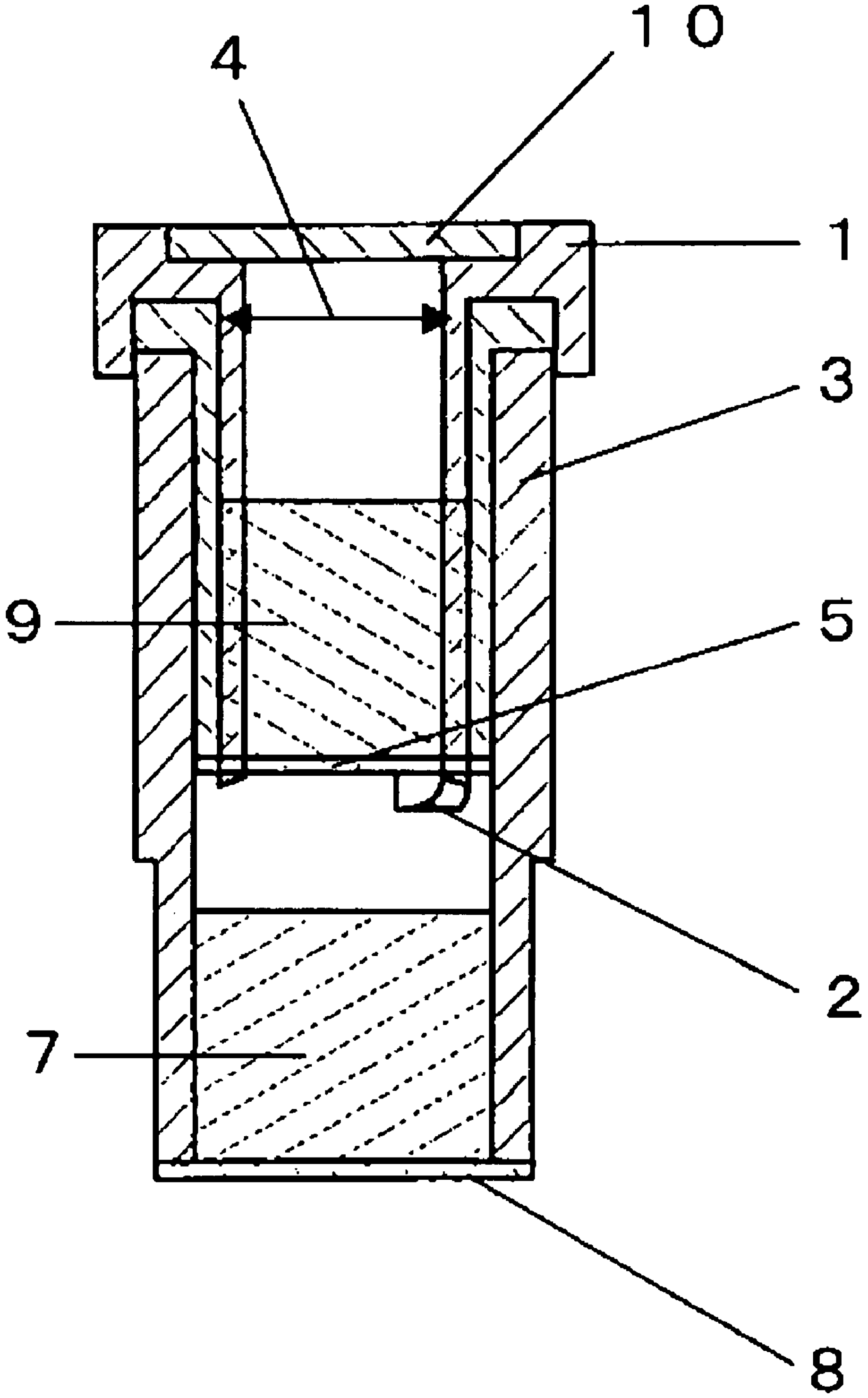
FIG. 5 is a side cross-sectional view of the test container of FIG. 1, in which an inlet is closed with a cap.

Then, the user closes the opening of the test container 3 with the cap 1. FIG. 5 shows a cross-sectional view of the test container 3 when the opening 4 is closed with the cap 1. As described above, in the opener 2 of the cap 1, a protrusion is provided on a tip thereof and, when the cap 1 is inserted into the test container 3, the opener 2 can be inserted in the state where it is adhered to the opening 4 of the test container 3. That is, at a position where a tip part of the opener 2 is inserted into the opening 4, the opening of the test container 3 has been already closed, and an internal space of the test container 3 is isolated from the outside. The isolated state used herein refers to the state where a virus accommodated in the test container 3 is not diffused to the outside, and an internal space of the test container 3 is breathable with a fine pore for introducing the outside air for making a cell in a sample alive. Further, a full length of the opener 2 is configured to be longer than a length from an upper end of the test container 3 to the first aluminum sheet 5 at a central part of the test container 3. Thereby, by inserting the cap 1 into the test container 3 until the jaw part 1*a* is abutted against an upper end surface of the test container 3, a protrusion of the opener 3 smashes the first aluminum sheet 5, and can break the first aluminum sheet 5. Further, in a middle part of the opener 2, that is, between initiation of insertion of a part other than the protrusion to arrival of the protrusion of the opener 2 at the first aluminum sheet 5, since the middle part of the opener 2 maintains the state where the part has been already adhered to the opening 4 over an entire circumference in a circumferential direction, the interior portion of the test container 3 is isolated from the outside. Therefore, upon mixing of a sample 9 and the reagent 7, the interior portion of the test container 3 is in the state where it is isolated from the outside, and a virus is not diffused to the outside. In addition, by the charcoal filter 10 provided on an upper side of the cap 1, breathability of the interior portion of the test container 3 is maintained without diffusion of a virus to the outside, and a cell contained in the sample 9 and a virus contained in the reagent 7 can be sufficiently reacted. Like this, by mixing the sample 9 and the reagent 7 in the interior portion of the test container 3, a measurement sample (reaction solution) is prepared.

The reaction solution prepared by the test container 3 as described above is supplied to a slide glass 11 explained later, and is tested with microscopic examination. A construction of the slide glass 11 will be explained below.

Figure 6:
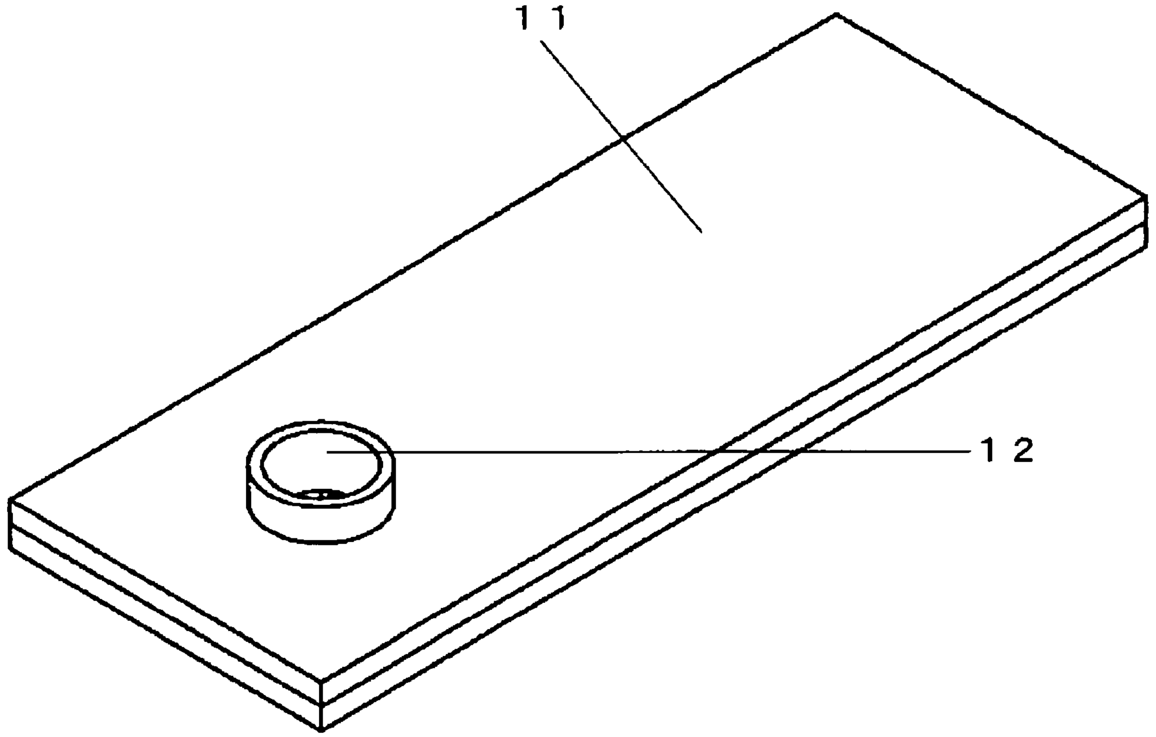
FIG. 6 is a perspective view showing a slide glass for microscopic examination which is one embodiment of the present invention.

FIG. 6 is a perspective view of the slide glass 11 for microscopic examination relating to one embodiment. The slide glass 11 of the present embodiment is a flat, and is of a rectangular parallelepiped plate, and has an insertion part 12 for inserting the test container 3 at a position near a short side from a central part of a plane of a rectangle. The insertion part 12 is of a cylinder having substantially the same size of an internal diameter as an outer diameter of the test container 3, and can be inserted through an opening at an upper part in the state where it is adhered to the test container 3 over an entire circumference. The test container 3 is inserted into this insertion part 12 from a bottom side having the second aluminum sheet 8.

Figure 7A:
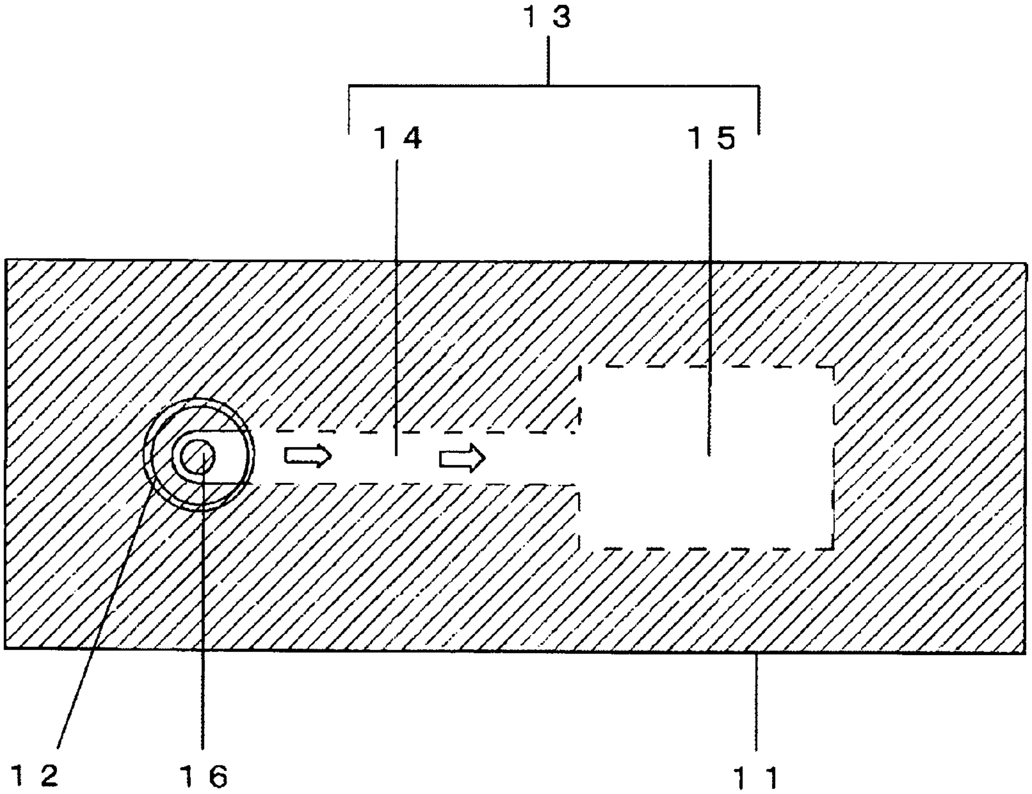
FIG. 7(*a*) shows a top view of the slide glass for microscopic examination shown in FIG. 6.
Figure 7B:
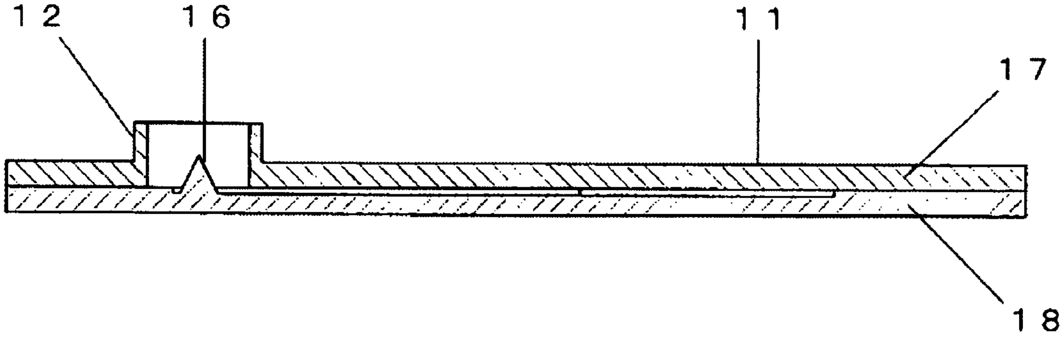

FIG. 7(*a*) shows a plane view of the slide glass 11, and FIG. 7(*b*) shows a cross-sectional view of a side thereof. The slide glass is constructed by fusing two slide glasses, a first slide glass 17 and a second slide glass 18. These first slide glass 17 and second slide glass 18 are fused so that water tightness is retained. In addition, as far as the first slide glass and the second slide glass are connected so as to retain water tightness, a connecting form is not limited, but for example, those slide glasses may be connected with an adhesive. In the first slide glass 17, an opening is provided, and the insertion part 12 is provided so as to stand up from a periphery of the opening (see FIG. 7(*b*)). In addition, in a place corresponding to the insertion part 12 of the second slide glass 18, a second opener 16 is provided. This second opener 16 is provided at a substantially central position of the insertion part 12, so as to be projected upwardly, and is approximately cone-like, an upper end being pointed. Thereby, the second aluminum sheet 8 provided on a bottom of the test container 3 which has been inserted into the insertion part 12 is smashed with the second opener 16, and a reaction solution which is a content is introduced into the slide glass 11.

At a part held by the first slide glass 17 and the second slide glass 18 of the slide glass 11, a holding part 13 for holding a reaction solution to be subjected to microscopic examination is provided. The holding part 13 of the slide glass 11 is constructed of a microscopic examination part 14 for microscopically examining a reaction solution, and a reaction sample passageway part 15 for guiding a reaction solution flown into the insertion part 12 to the microscopic examination part 14. The microscopic examination part 14 is formed as a flat space so that a supplied reaction solution can be observed by microscopic examination.

Then, a motion of use of the kit for cancer cell test relating to an embodiment of the present invention will be explained. First, a user injects a sample, and inserts the test container 3 in the state where an opening is closed with the cap 1, into the insertion part 12 of the slide glass 11. Thereby, the second aluminum sheet is broken with the second opener 16, and a reaction solution accommodated in the test container 3 is supplied to the insertion part. Thereby, as shown in an arrow of FIG. 7(*a*), the reaction solution is flown in the reaction sample passageway part 15 to reach the microscopic examination part 14. In addition, as described above, since the insertion part 12 and the test container 3 can be inserted in the state where they are adhered without excess and deficiency, the holding part 13 is brought into the state where it is isolated from the outside, by insertion into the insertion part 12 of the test container 3. Further, since a tip of the second opener 16 is positioned below an entrance upper side of the insertion part 12, upon breaking of the second aluminum sheet 8 with the second opener 16, the holding part 13 has been already brought into the state where it is isolated from the outside, that is, the state where a reaction solution containing a virus is isolated from the outside. With this construction, the virus in the reaction solution is not diffused to the outside also at microscopic examination, and diagnosis can be implemented safely.

An example of specific embodiments has been explained, but the present invention is not limited to these embodiments, and a variety of variations are possible.

The sample in the present invention is not particularly limited as far as it contains a cell derived from a living body collected from a subject, but examples include samples from blood, sputum and uterus. Particularly, samples of blood, sputum and uterus are preferable.

The virus used in the present invention is not particularly limited as far as it has the ability to infect a cell in a sample, but an oncolytic virus is exemplified, and specifically d12.CALP, d12.CALP delta RR, Telomelysin, Telomelysin-RGD, AxE1AdB-UPRT, AdSLP1.E1AdB, AxE1CAUP, AdE3-IAI.3B, Ad-MKAdMK, AdCEAp/Rep, AdAFPep/Rep, MMP-sub II SeV/delta M, or CD-MMP-sub II-SeV/delta M are preferable.

The seal part and the second seal part in the present invention are not particularly limited as far as a reagent containing a virus is not flown to the outside, and the virus is not diffused to the outside, but examples include an aluminum sheet.

The virus-impermeable breathable filter used in the present invention is not particularly limited as far as it dose not diffuse a virus in a reaction solution to the outside, and has breathability, but examples include a breathable anti-virus filter and a virus-adsorbable filter. Specifically, a charcoal filter is preferable.

Isolation in the present invention is not particularly limited as far as it is the state where a virus in not diffused to the outside, and a position with breathability rather than the complete closed state is preferable because a cell in a sample and a virus in a reagent can be reacted sufficiently.

The kit for preparing a cancer cell detection sample in the present invention is not particularly limited in its use as far as it is a test by which a cancer cell can be confirmed, and examples include a microscopic examination test and a test with a flow cytometer.

A variety of characteristics shown in the aforementioned embodiments can be combined mutually. When a plurality of characteristics are included in one embodiment, one or a plurality of characteristics among them can be appropriately extracted, and they can be adopted alone or in combination, in the kit for preparing a cancer cell detection sample, and the kit for cancer cell detection using the same, of the present invention.

EXAMPLES

The present invention will be specifically explained below using Examples, by referring to results of a method for detecting cancer which actually uses the kit for cancer cell detection of the present invention.

Example 1

Detection of Lung Cancer Cell (Preparation of Sample)

A sputum collected from a healthy person was recovered into 1.5 ml of a cell culturing solution (Dulbecco's Modified Eagle Medium; DMEM), and pre-culturing was performed under the condition of 37° C. and 5% $CO_2$ for 60 minutes. The pre-cultured cell culturing solution was diluted with DMEM to $1.0\times10^6$ cells/ml, and to this was added a solution of an A431 cell (purchased from ATCC) which is a human lung cancer cell strain to 1000 cells/300 µl, and this was used as a lung cancer sample.

Separately, as a control, a cell culturing solution ($1.0\times10^6$ cells/ml) before addition of an A431 cell solution, and an A431 cell solution which had been diluted with DMEM to 1000 cells 300 µl were prepared.

(Preparation of Reagent)

A reagent containing OBP-301 which is an oncolytic virus encoding a green fluorescent protein (GFP) was prepared by a known method described in CANCER RESEARCH 64, 6259-6265, Sep. 1, 2004. The prepared reagent was sealed into the reagent inclusion part 6 of the aforementioned test container 3.

(Virus Infection on Sample)

Each 250 µl of the control or the cancer sample was injected into the test container 3 in which the reagent containing OBP-301 was sealed into the reagent inclusion part 6 of the aforementioned kit for preparing a cancer cell detection sample. Thereafter, the cap 1 was inserted until the jaw part 1*a* was abutted against an upper end of the test container 3, and culturing was performed under the condition of 37° C. and 5% $CO_2$ for 24 hours, thereby, the sample was infected with a virus.

(Observation of Sample)

Figure 8:
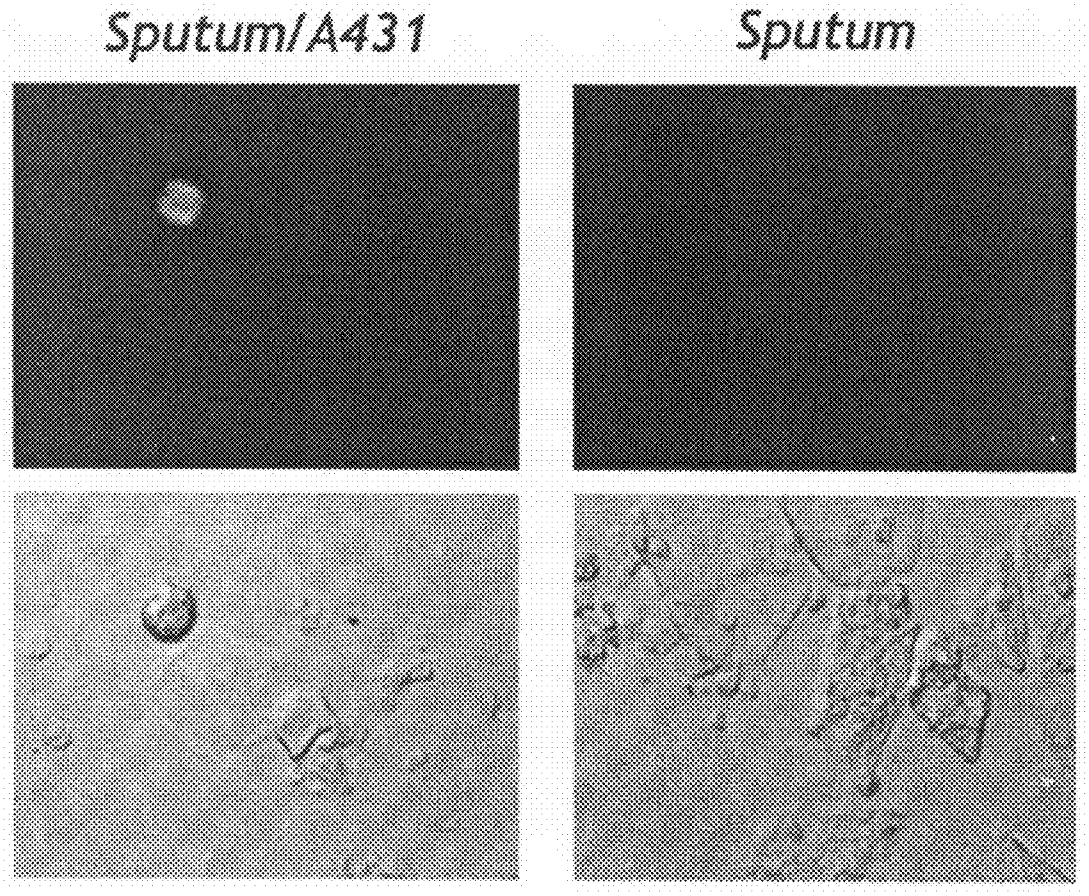
FIG. 8 is a view showing a result of an observation of a lung cancer cell with a fluorescent microscope.

The test container 3 after virus infection was inserted into the insertion part 12 of the aforementioned slide glass 11, and a reaction solution held by the microscopic examination part 14 was observed with a fluorescent microscope, and the results are shown in Table 1 and FIG. 8.

TABLE 1

| | Number of GFP-expressing cells | | | GFP expression efficiency (%) |
|---|---|---|---|---|
| Sputum | 0 | 0 | 0 | |
| Sputum/A431 | 223 | 231 | 236 | 92.0 ± 2.6 |
| A431 | 243 | 244 | 237 | 96.5 ± 1.5 |

Sputum indicates a cell culturing solution ($1.0\times10^6$ cells/ml) before addition of an A431 cell, Sputum/A431 indicates a lung cancer sample, and A431 indicates an A431 cell solution which has been diluted with DMEM to 1000 cells/300 µl.

Example 2

Detection of Uterine Cervical Cell (Preparation of Sample)

Using a sterilized swab, an oral cavity mucosa cell was recovered into 10 ml of a cell culturing solution (Dulbecco's Modified Eagle Medium; DMEM), and this was pre-cultured under the condition of 37° C. and 5% $CO_2$ for 60 minutes. The pre-cultured cell culturing solution was diluted with DMEM to $1.0\times10^6$ cells/ml, and to this was added a Hela cell solution (purchased from ATCC) which is a human lung cancer cell strain to 1000 cells/300 µl, and this was used as a uterine cervical sample.

Separately, as a control, a cell culturing solution ($1.0\times10^6$ cells/ml) before addition of a Hela cell solution, and a Hela cell solution which had been diluted with DMEM to 1000 cells/300 µl were prepared.

Figure 9:
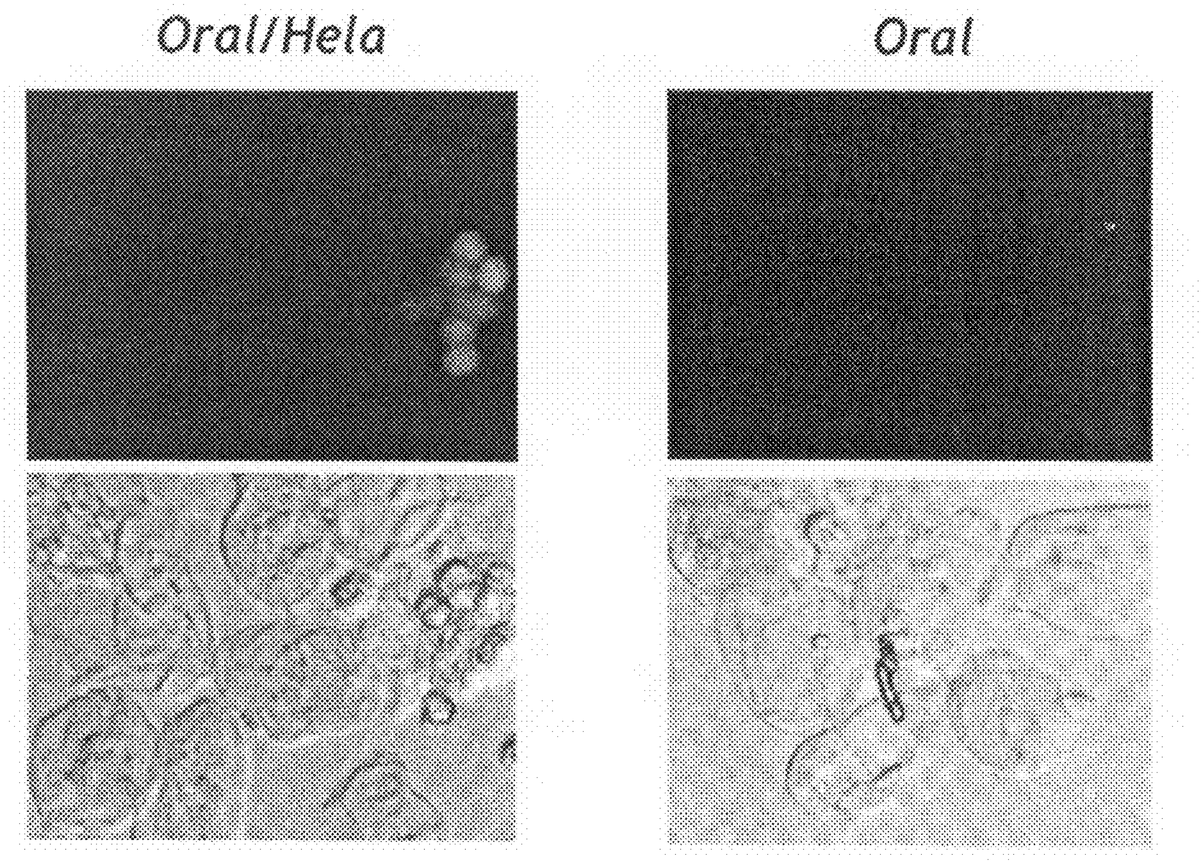
FIG. 9 is a view showing a result of an observation of a uterine cervical cell with a fluorescent microscope.

According to the same procedure as that of Example 1 except for the aforementioned procedure, the sample was observed. The results are shown in Table 2 and FIG. 9.

TABLE 2

| | Number of GFP-expressing cells | | | GFP expression efficiency (%) |
|---|---|---|---|---|
| Oral | 0 | 0 | 0 | |
| Oral/HeLa | 198 | 209 | 213 | 82.7 ± 3.1 |
| HeLa | 245 | 238 | 227 | 94.7 ± 3.6 |

Oral indicates a cell culturing solution ($1.0\times10^6$ cells/ml) before addition of a Hela cell, Oral/Hela indicates a uterine cervical sample, and Hela indicates a Hela cell solution which has been diluted with DMEM to 1000 cells/300 µl.

As apparent from Examples, a cancer cell can be actually detected using the kit for preparing a cancer cell detection sample of the present invention, and the kit for cancer cell detection using the same.

The foregoing detailed description and examples have been provided by way of explanation and illustration, and are not intended to limit the scope of the appended claims. Many variations in the presently preferred embodiments will be obvious to one of ordinary skill in the art, and remain within the scope of the appended claims and their equivalents.

What is claimed is:

1. A kit for preparing a detection sample for detecting a cancer cell, comprising:

a test container having an opening for receiving a biological sample collected from a subject, a biological sample inclusion part, a reagent inclusion part comprising a reagent containing a virus, a seal part for sealing the reagent inclusion part of the test container from the biological sample inclusion part, a cap for closing the opening, and an opener for breaking the seal part.

2. The kit for preparing a detection sample according to claim 1, wherein the cap has a virus-impermeable breathable filter.

3. The kit for preparing a detection sample according to claim 1, wherein the opener is capable of breaking the seal part accompanying an action of closing the opening by the cap.

4. The kit for preparing a detection sample according to claim 1, wherein the cap has the opener.

5. The kit for preparing a detection sample according to claim 1, wherein the virus in the reagent inclusion part is isolated from the outside when the opener breaks the seal part.

6. The kit for preparing a detection sample according to claim 1, wherein the cap and the opener are integrally configured, the opener has a leading edge for breaking the seal part, and a middle part for connecting the cap and the leading edge, and the middle part is attached firmly to an inner side surface of the test container by inserting the middle part into the test container through the opening.

7. The kit for preparing a detection sample according to claim 1, wherein a genome of the virus comprises a promoter of a carcinogenic gene and a gene encoding a target protein.

8. The kit for preparing a detection sample according to claim 1, wherein the virus is an oncolytic virus.

9. The kit for preparing a detection sample according to claim 1, wherein the virus is d12.CALP, d12.CALP delta RR, Telomelysin, Telomelysin-RGD, AxE1AdB-UPRT, AdSLP1.E1AdB, AxE1CAUP, AdE3-IAI.3B, Ad-MKAdMK, AdCEAp/Rep, AdAFPep/Rep, MMP-sub II SeV/delta M, or CD-MMP-sub II-SeV/delta M.

10. The kit for preparing a detection sample according to claim 1, wherein the sample is collected from blood, sputum or uterus.

11. A method for diagnosing cancer, comprising using the kit for preparing a detection sample as defined in claim 1.

12. The diagnosis method according to claim 11, wherein the cancer is blood cancer, lung cancer or uterine cervical cancer.

13. A kit for detecting a cancer cell, comprising:

a kit for preparing a detection sample for detecting a cancer cell comprising:

a test container having an opening for receiving a biological sample collected from a subject, a biological sample inclusion part, a reagent inclusion part comprising a reagent containing a virus, a seal part for sealing the reagent inclusion part of the test container from the biological sample inclusion part, a cap for closing the opening, an opener for breaking the seal part, and a second seal part located on the bottom of the test container;

and a glass slide comprising:

an insertion part for inserting the test container, a second opener for breaking a bottom seal of the test container by an action of inserting the test container into the insertion part, and a holding part for guiding a reaction solution comprising the biological sample and the reagent from the test container into a viewing area of the glass slide when the bottom seal is broken with the second opener.

14. The kit for cancer cell detection according to claim 13, wherein the cap has a virus-impermeable breathable filter.

15. The kit for cancer cell detection according to claim 13, wherein the opener breaks the seal part accompanying with an action of closing the opening with the cap.

16. The kit for cancer cell detection according to claim 13, wherein the virus in the interior portion is isolated from the outside when the second opener breaks the bottom of the test container.

17. The kit for cancer cell detection according to claim 13, wherein the bottom of the test container has a second seal part which is broken with the second opener.

18. A method for diagnosing cancer, comprising using the kit according to claim 13 for detection.

19. The diagnosis method according to claim 18, wherein the cancer is blood cancer, lung cancer or uterine cervical cancer.

* * * * *